United States Patent
Reif et al.

(10) Patent No.: US 8,778,374 B2
(45) Date of Patent: Jul. 15, 2014

(54) BONE FORMATION AGENT AND METHOD OF PRODUCTION

(75) Inventors: Dieter Reif, Frankfurt/Main (DE); Ute Reif, legal representative, Frankfurt/Main (DE); Fabian Peters, Frankfurt/Main (DE); Frank Palm, Frankfurt/Main (DE); Joachim Wittner, Frankfurt/Main (DE)

(73) Assignee: Curasan AG, Frankfurt/Main (DE)

(*) Notice: Subject to any disclaimer, the term of this patent is extended or adjusted under 35 U.S.C. 154(b) by 2147 days.

(21) Appl. No.: 10/561,800

(22) PCT Filed: Jun. 25, 2004

(86) PCT No.: PCT/EP2004/006947
§ 371 (c)(1),
(2), (4) Date: Nov. 13, 2006

(87) PCT Pub. No.: WO2004/112855
PCT Pub. Date: Dec. 29, 2004

(65) Prior Publication Data
US 2007/0218098 A1    Sep. 20, 2007

(30) Foreign Application Priority Data
Jun. 26, 2003 (DE) .................. 103 28 892

(51) Int. Cl.
*A61F 2/00* (2006.01)
*A61F 13/00* (2006.01)
*C04B 35/447* (2006.01)

(52) U.S. Cl.
USPC .......... 424/423; 424/422; 424/426; 523/113; 523/115; 523/116

(58) Field of Classification Search
None
See application file for complete search history.

(56) References Cited

U.S. PATENT DOCUMENTS

| 4,629,464 A | 12/1986 | Takata et al. |
| 6,210,715 B1 * | 4/2001 | Starling et al. ............... 424/489 |

(Continued)

FOREIGN PATENT DOCUMENTS

| DE | 35 31 144 | 3/1986 |
| DE | 29922585 | * 8/2000 |

(Continued)

OTHER PUBLICATIONS

Trisi et al, Histologic Effect of Pure-Phase Beta-Tricalcium Phosphate on Bone Regeneration in Human Artificial Jawbone Defects, J Periodontics Restorative Dent 2003; 23:69-77.*

(Continued)

*Primary Examiner* — Cherie M Stanfield
(74) *Attorney, Agent, or Firm* — Roylance, Abrams, Berdo & Goodman, L.L.P.

(57) ABSTRACT

The invention relates to a bone formation agent of porous calcium phosphate having an isotropic sintered structure and, between the particles of the calcium phosphate, statistically distributed pores in a plurality of discrete size ranges. The bone formation agent has at least two, preferably three, discrete pore size distributions. Its porosity has an irregular geometric shape. The sintered particles of the calcium phosphate have a particle size smaller than 63 μm with a $d_{50}$ value in the range from 5 to 20 μm. The interconnecting pore share in the overall porosity is limited to pore sizes less than 10 μm. The bone formation agent can be used in the form of a granulate or shaped body for bone regeneration. In the case of granulates, the maximum pore diameters are matched to the granulate diameter. The invention relates also to a method of producing the bone formation agent.

16 Claims, 7 Drawing Sheets

(56) References Cited

U.S. PATENT DOCUMENTS

| | | |
|---|---|---|
| 6,521,246 B2 * | 2/2003 | Sapieszko et al. ............ 424/423 |
| 2005/0027367 A1 * | 2/2005 | Heide et al. ................. 623/23.5 |

FOREIGN PATENT DOCUMENTS

| | | |
|---|---|---|
| EP | 1 197 233 | 4/2002 |
| EP | 1293220 | 11/2006 |
| JP | 07-124241 | 5/1995 |
| JP | 2001-054565 | 2/2001 |
| WO | WO 92/21302 | 12/1992 |
| WO | WO 98/15505 | 4/1998 |
| WO | WO 00/42991 | 7/2000 |
| WO | WO 02/083194 | 10/2002 |

OTHER PUBLICATIONS

English language machine translation of JP-07-124241 (May 16, 1995 publication date).*

* cited by examiner

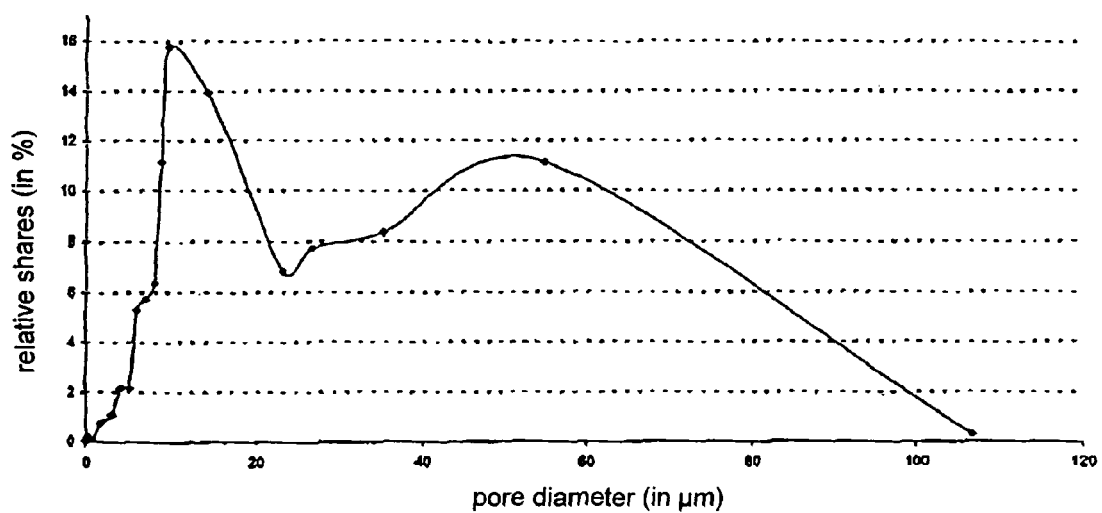
Figure 7: Pore size distributions (I) and (II) in the pore diameter range < 100 μm, measured by means of mercury porosimetry

BONE FORMATION AGENT AND METHOD OF PRODUCTION

The invention relates to a synthetic, bioresorbable bone formation agent for the treatment of bone defects in the human or animal skeleton. The agent is used for the temporary filling of a bone defect; it forms a guideway for the regeneration of bone in the defect, simultaneously being resorbed by the body within a clinically reasonable period for the formation of new bone.

In addition to bone replacement agents and bone formation agents of biological origin, synthetic biomaterials for filling bone defects have also been known for many years. In particular, calcium phosphates have become established as an important group of substances for that application area. Because of the chemical similarity with the mineral constituent of bone, special importance is attached, in particular, to materials having a hydroxyapatite structure in sintered, but also non-sintered, form as a granulate or in the form of solid shaped pieces. Above all, amongst the non-resorbable implants, so-called "bioactive glass-ceramics" have, in the past 20 years, extended the range of bone replacement materials.

In general terms it can be stated that the development of bioceramics and comparable materials has gone in two directions, each of which has its justification with regard to clinically relevant indications: materials which have long-term stability in the body and are distinguished by good hydrolytic resistance with respect to body fluid, and biodegradable materials which in part are slowly dissolved in body fluid and in part are subjected to cellular breakdown without triggering appreciable foreign-body reactions.

The latter group of materials, in particular, has become increasingly important as a bone regeneration approach which is based on restoring the original natural state of the bone before the defect was formed, a process which is referred to as "restitutio ad integrum". In the process, formation of new bone and bioresorption/biodegradation of the bone formation agent proceed simultaneously in such a way that the bone formation agent temporarily fills the defect, promotes growth of bone in the defect as an osteoconductive guideway and at the same time is resorbed by the body at a rate that is optimally matched to the rate of formation of new bone, so that on the one hand the bone formation agent can fully bring into play its osteoconductive properties without on the other hand forming a barrier to the growth of new bone. The better the two processes are matched, the more highly a bone formation agent must be rated in qualitative terms.

The regenerative capability of a bone formation agent is not governed solely by its material composition. Even substances of identical chemical composition can exhibit a markedly different regeneration potential, the reason for that different behaviour generally lying in the microstructure of the biomaterial. Accordingly, the importance of an interconnecting microporosity is now recognised, as well as the role of macropores within a bioceramic for successful integration of the material into bone and also for its resorption characteristics. In that regard the prior art is currently represented by bioceramics which have micro- and macro-porous sintered structures reaching overall porosities of at least 50% by volume.

However, a large number of described inventions have already proceeded to still higher overall porosities. EP 0267624 describes a calcium phosphate-based bone replacement material which, with an overall porosity of up to 75%, has open and closed pores, with particular importance being attached to the open pores with respect to the foreign-body reaction of the implant. In particular, pores in the diameter range from 0.01 to 50 µm according to one observation should result in the body's own defence cells no longer identifying the material as a foreign body. The average size of the open pores can span a wide range from 0.01 to 2000 µm.

A microporous bone prosthesis material produced from porous calcium phosphate is protected by DE 3717818. The particles of porous calcium phosphate have open cells equal to or larger than 0.01 µm and smaller than 10 µm. The overall porosity can be up to 90%. Underlying this material too is the observation that adhering macrophages do not identify the material as a foreign body when it is adequately rinsed through by body fluid.

According to DE 29922585, a temporary bone defect filler is claimed which is characterised by interconnectingly linked micropores having an average size in the range from 0.5 to 10 µm and having a share of from 20 to 50% in the overall porosity and by macropores, at least some of which are interconnectingly linked, having an average size in the range from 50 to 1000 µm and having a share of from 50 to 80% in the overall porosity, the non-interconnectingly linked macropores being linked to their neighbours by way of micropores, the macropores having a typically polyhedral shape and the overall porosity being >50% by volume.

A calcium phosphate-based bone replacement material having a porosity of from 40 to 90%, which is protected by DE 3425182, has spherical pores, those substantially spherical pores being in the size range from 3 to 600 µm and being linked to one another and to the surface of the shaped body by capillary pore channels having a diameter from 1 to 30 µm. The pore channels are achieved by means of an addition of organic fibres to the starting mixture.

A bone replacement material in accordance with DE 19581649 T1 also has spherical pores with, at the same time, concave depressions being present on the surface of the implant for stimulating bone growth. The average pore diameters of the spherical pores are in the range from 300 to 2000 µm. At least some of the macropores are interconnectingly linked. Additional micropores are not described.

According to WO 01/13970 A1 and DE 19940717 A1, protection is claimed for shaped parts of a resorbable bone replacement and bone formation material of porous beta-TCP which have an interconnecting microporosity and a defined macroporosity in the form of tubular pores introduced by machining. The tubular pores are preferably oriented in the bone growth direction.

U.S. Pat. No. 6,521,246 protects inorganic shaped bodies of calcium phosphate for use in bone healing in living organisms, having a substantially uniform macro-, meso- and micro-porosity with an overall porosity of at least 30%, and also methods of production. Macroporosity is understood therein to refer to pores equal to or larger than 100 µm, mesoporosity to pores having diameters between 10 and 100 µm and microporosity to pores smaller than 10 µm. The overall porosity of all pores can be up to 95%.

According to WO 02/083194, protection is claimed for an osteoconductive or osteoinductive biostructure comprising interconnected particles. The particles form a matrix, which has at least one porous portion and which can consist of up to three structural types. The basic structure is a microstructure having a unimodal pore size distribution with an average pore size of between 10 and 50 µm. The further mesostructure and macrostructure structural types can be added thereto by means of 3D printing technology. A biostructure having a plurality of structural types then has a bimodal pore size distribution. In accordance with WO 02/083194, a biostructure is understood to be a shaped body having precisely defined structural features, produced by means of 3D printing technology.

A method of producing a similar shaped body is protected by WO 00/42991. The shaped body produced by that method has a substantially uniform macro-, meso- and micro-porosity with an overall porosity of at least 30%. Further protection is claimed for a method of bone regeneration using a shaped body having an overall porosity of at least 50%.

A further porous bioceramic shaped body is protected in accordance with EP 1197233, that being a shaped body of foamed calcium phosphate. Spherical pores are produced in the ceramic microstructure, so that in a number of implementation examples a bimodal pore size distribution was measured by means of mercury porosimetry.

According to WO 98/15505, protection is claimed for a method of producing porous bioceramic articles which likewise uses a foaming method, the ceramic foam formed being stabilised by means of polymerisation of a monomer and the articles being fired in order to remove the organic constituents and to sinter the ceramic particles together.

WO 92/21302 claims protection for a porous implant consisting of zones of differing porosity, the surface of the implant having macropores in the range from 50 to 500 µm to assist growing-together with bone.

From DE 3531144 there is known a porous hydroxyapatite material which, for filling a bone defect, is used in the form of a granulate having an open microporosity with a pore size distribution in the range from 10 to 100 µm and with an overall porosity in the range from 20 to 50% and which in the form of an implant has a pore size distribution in the range from 200 to 2000 µm. When subject to high mechanical demands, the implant can additionally have a surface layer of microporous material.

According to the prior art it is to be assumed that the regeneration potential of a bone formation agent is consequently governed to a substantial extent by the specific morphology of its porosity. Whilst an interconnecting micropore network primarily ensures the biocompatibility of the material, interconnecting macropores in a size range from 100 to 500 µm primarily promote bone growth through the material. It seems to be immaterial whether the material is of synthetic or bovine origin or whether it is a bioresorbable or non-bioresorbable bone formation agent.

In the case of resorbable bone formation agents, the macropores bring about the further advantage that, as a result of the reduction in material density per defect volume, a smaller amount of material has to be resorbed, which, on the one hand, reduces the load on the patient's metabolism and, on the other hand, even brings about a reduction in the time that the resorption process takes. Subsequent treatments such as the insertion of tooth implants after filling of the alveoli with a bioresorbable bone formation agent are accordingly possible at an earlier point in time, which is entirely to the benefit of the patient.

On their own, however, the structural features of porosity mentioned in the prior art are not fully sufficient for specifying a bioresorbable bone formation agent. The strength of its sintered structure, that is to say the strength of the sintered contact points between the powder particles of the bone formation agent subjected to sintering, and the size thereof are further important features governing its biocompatibility. The so-called sintering necks between the ceramic particles must have a mechanical stability such that the sintered structure is preserved at least over the wound-healing phase in the first weeks postoperatively and the structure of the bone formation agent does not break down into particles on contact with body fluid. If such an event occurs and the sintered particles of calcium phosphate have a particle size of <10 µm, they will trigger foreign-body reactions in addition to the inflammation processes associated with wound healing, which foreign-body reactions can delay or impede the bone healing process.

By extension this also applies to non-sintered materials, only in that case the particles are fixed by other mechanisms such as polymer binding (DE 19614421 A1) or masking by a xerogel (e.g. WO 01/54747 A1). In those cases too, spontaneous release of particles must be avoided for the reasons mentioned or such release must be limited to a clinically tolerable amount of particles insufficient to cause acute inflammation reactions.

A further important quality criterion for a sintered bone formation agent is consequently a stable sintered structure having strong sintering necks from one calcium phosphate particle to another, which allow release of particles only in conjunction with the resorption process. However, it is not always the case that particles released during resorption are free from concern. As has been found by Klein et al., particles of low solubility can be carried off by phagocytes and deposited in the body's lymphatic system (Biomaterials, 6(1985) 189-192). There are as yet no firm findings relating to the long-term effect of such crystalline particles in the lymph nodes. Such cases occur especially when, because of inadequacies in the production method, bioresorbable bone formation agents are not produced in a pure phase form and contain phase constituents which are not bioresorbable or are bioresorbable only with difficulty. This was found especially in the initial period of using beta-tricalcium phosphate for bone defect filling. Deviations from the stoichiometry or inappropriate process implementation resulted in considerable levels of hydroxyapatite as a foreign phase in the tricalcium phosphate. Because of its low solubility in the sintered state, hydroxyapatite remains behind in particle form in the course of the resorption of the tricalcium phosphate, is carried away from the defect by phagocytes and is then found, as the investigations by Klein et al. show, in the surrounding lymph nodes.

This means that, when assessing the quality of the bone formation agent beta-tricalcium phosphate in particular, the degree of phase purity is a further important criterion. In view of the above-described risks, even if ASTM F 1088-87 (Reapproved 1992) "Standard Specification for Beta-Tricalcium Phosphate for Surgical Implantation" allows a hydroxyapatite content of less than/equal to 5% by weight in the beta-tricalcium phosphate, the lower the content of that foreign phase, the higher is the assessment to be given to a beta-tricalcium phosphate.

Modern manufacturing methods currently allow beta-tricalcium phosphate to be produced with a phase purity in respect of hydroxyapatite that is better than 99% by weight, that is to say with a content of that phase which is clearly below 1% by weight. Such substantially pure-phase products are always to be preferred for implantation applications in the human body over those with a clearly demonstrable hydroxyapatite content, in order to rule out the mentioned risks.

Of course, the chemical composition of a bioresorbable bone formation agent plays a decisive role in respect of its resorption rate. Amongst synthetic bioresorbable bone formation agents, tricalcium phosphate above all—especially beta-tricalcium phosphate—has come to the fore in the last 10 to 15 years. WO 91/07357 describes, inter alia, bone formation agents of improved resorbability. The objective consists of a reduction in resorption time with simultaneous acceleration of bone regeneration. The materials for which protection is claimed consist of chemically modified tricalcium phosphate wherein some of the calcium ions have been replaced by other cations in order to improve solubility.

The fact that the chemical composition of the bone formation agent is not solely responsible for its regeneration properties can be seen very clearly in the particular case of tricalcium phosphate. Depending on the production conditions, tricalcium phosphate having the empirical formula $Ca_3(PO_4)_2$ can be produced in two different crystalline forms, a high-temperature or alpha form and a low-temperature or beta form. Chemically, there is no difference at all between the two forms. However, the two forms behave entirely differently when in contact with body fluid despite having otherwise identical features such as sintered structure, porosity, size of sintered particles and strength of sintering necks. The high-temperature form alpha-TCP, which is metastable at room temperature, constitutes a relatively high-energy configuration which, for energy-related reasons and because of its crystallographic similarity, transforms itself into hydroxyapatite when in contact with body fluid (Lin et al., Biomaterials, 22 (2001) 2990). Because of the lower solubility of hydroxyapatite, this phase transformation markedly extends the resorption time of alpha-TCP, even though it is ascribed a higher solubility than beta-TCP (Lin et al., Biomaterials, 22 (2001) 2981). The low-temperature form beta-TCP, which is relatively stable in energy terms, does not exhibit this phase transformation and is therefore resorbed more quickly than the alpha form assuming a comparable sintered structure, pore structure and implant bed activity.

The known agents for the regeneration of bone defects are above all described with a view to improvement of their sintered structure and pore structure in the granulate particle. A trend towards higher and higher porosities is observed here, the overall porosities of granulates being composed of microporosity and macroporosity components. Microporosity is understood to refer to pore size distributions <10 µm, whereas macroporosity starts at pore sizes above 100 µm. The current state and development of micro- and macro-porous bone regeneration agents is characterised by an increasing macropore component, which weakens the mechanical stability of the sintered structures ever further. For such bone regeneration agents this results in an ever greater risk that they will not withstand the mechanical stresses of transportation and introduction into the defect, breaking down into particles and even possibly triggering foreign-body reactions as a result.

The particle shape of the granulate can have various geometries. Above all, spherical, egg-shaped and polygonal shapes are known. For practical clinical use, the granulates are usually provided in particle bands from 50 to 2000 µm and—in individual cases—above. For particular indications, the particle band is sub-divided further, for example 50 to 150 µm, 150 to 500 µm, 500 to 1000 µm and 1000 to 2000 µm.

Limits in respect of strength are set which prevent material porosities from being increased at will; this limits further reduction of the amount of bone formation agent per defect volume. The higher the overall porosity in the form of micropores and macropores is pushed, the lower the mechanical strength of the granulate particles. On no account should introduction of the granulate into the defect or mixing of the granulate with, for example, the patient's own blood or PRP (platelet rich plasma) cause destruction of the granulate structure. This sets limits on the overall porosity of a bone formation agent because such destruction of the structure will, on account of fine particle formation, result in bone healing problems due to foreign-body reactions.

In addition, information from clinical practice indicates a situation in the case of calcium phosphate ceramics having interconnecting macropore systems which has attracted little attention hitherto. In the granulate particles, an at least partly interconnecting macropore system accessible from the surface can, according to that observation, form a refuge for micro-organisms and increase the risk with respect to successful bone regeneration in the defect. If micro-organisms gain access to such locations, they are inaccessible—or accessible only with difficulty—to systemic treatment with antibiotics (Palm, F.: Calcium phosphate ceramics as a bone substitute material—A prospective clinical trail. IMOI, submitted).

The aim of the invention is to improve the prior art, especially to ensure adequate mechanical strength of the bone formation agent whilst having a high overall porosity and to reduce risks in problem defects.

The invention is based on the problem of improving bone regeneration of the defect by means of a new porosity and sintering design without interconnecting macroporosity whilst ensuring that the bone formation agent has the specified mechanical strength sufficient for bone defect filling.

The problem according to the invention is solved by provision of a new bone formation agent of porous calcium phosphate having an isotropic sintered structure and, between the sintered particles of the calcium phosphate, statistically distributed pores in a plurality of discrete size ranges. The bone formation agent has a porosity having an irregular polygonal geometric shape and has at least two discrete pore size distributions (I) and (II) having clear maxima. The size of the calcium phosphate particles sintered together is smaller than 63 µm with a $d_{50}$ value in the range from 5 to 20 µm. The pores form the empty space between the particles of calcium phosphate, the interconnecting pore share being limited to pore sizes less than 10 µm.

In accordance with the invention, the maxima of the two discrete pore size distributions (I) and (II) are in a range from 0.5 to 10 µm for pore size distribution (I) and 10 to 100 µm for pore size distribution (II).

A particular embodiment of the invention preferably has three maxima of pore size distributions (I), (II) and (III). In that case, the maxima of the pore size distributions are at pore diameters in the ranges from 0.5 to 10 µm for pore size distribution (I), 10 to 100 µm for pore size distribution (II) and 100 to 5000 µm for pore size distribution (III).

Compared to the prior art, the selected size of the sintered particles of calcium phosphate, at <63 µm and a $d_{50}$ value of from 5 to 20 µm, has been selected to be relatively large so that more than 50% of the particles are above the size accessible to macrophages (<5 µm). In addition to a strong ceramic bond resulting from stable sintering necks, this provides an additional safeguard to prevent foreign-body reactions.

In order to accelerate the resorption process, the prior art attempts to reduce the material provided per defect volume by producing a large number of, as far as possible, interconnecting macropores in a size range from 100 to 2000 µm which is of relevance to the growing-in of bone. However, an increasing number of macropores on the one hand has an adverse effect on the strength of the material and on the other hand increases the risk associated with use of the bone formation agent in so-called problem defects. In contrast, in accordance with the invention an interconnecting macropore network is eliminated and an upper limit of 10 µm is placed on the sizes/channel cross-sections of an interconnecting pore system. At the same time, as a result of modification of the production method, an improvement in the strength of the sintering necks is obtained.

It is characteristic of the bone formation agent according to the invention that the ratio of the amounts of pores in the three pore size distributions can be adjusted in line with requirements and matched to the intended use. The adjustment of that ratio of the amounts of different pore sizes also prevents the level of statistical pores of pore size distribution (III) from increasing above a certain level and prevents these pores from possibly becoming interconnecting. Besides or instead of statistical pores of pore size distribution (III), a defined porosity in the form of tubular pores can additionally be provided in shaped bodies of defined geometric dimensions. These tubular pores are introduced by machining. They may be oriented in one, two or three spatial directions and usually extend from one surface of the shaped body to the opposite surface. Tubular pores in one spatial orientation are preferably arranged in parallel. When they are oriented in a plurality of spatial directions, they form right angles with one another and can cross. Preference is given to the tubular pores being arranged in the bone growth direction.

In order to obtain optimum properties of the bone formation agent, the volume shares of pore size distributions (I) to (III) in the overall porosity are within particular percentages. For good material strength whilst ruling out interconnecting macroporosity there have been found to be advantageous: for pore size distribution (I) a share in the range from 20 to 40% by volume, for pore size distribution (II) a share in the range from 5 to 40% by volume and for pore size distribution (III) a share in the range from 1 to 40% by volume, the overall porosity being limited to 85% by volume in order to ensure sufficient strength in use.

In accordance with this approach, pores of pore size distributions (II) and (III) are linked to one another and to the surface solely by way of the interconnecting pore system (I) so that it is impossible for the interior of the bone formation agent to be colonised by micro-organisms and consequently for the latter to be able elude systemic treatment with antibiotics.

The bone formation agent according to the invention can be made from any desired materials suitable for bone regeneration but preferably consists to a substantial extent, and especially to an extent of at least 95%, of a calcium phosphate from the group alpha-tricalcium phosphate, beta-tricalcium phosphate, octacalcium phosphate, alkali metal-modified and/or alkaline earth metal-modified tricalcium phosphate, calcium diphosphate, carbonate apatite of type B and calcium-deficient hydroxyapatite or mixtures thereof. A particular embodiment of the invention relates to a bone formation agent of calcium phosphate, preferably beta-tricalcium phosphate having a phase purity of 99% or more than 99% by weight, relative to the foreign hydroxyapatite phase.

The bone formation agent according to the invention can be used in the form of suitable granulates for bone defect filling. Usual particle size distributions for such granulates are in the range from 50 to 10000 μm, preferably in the range from 50 to 8000 μm. Generally, particle size ranges that are narrower for particular indications, for example 50 to 150 μm, 150 to 500 μm, 500 to 1000 μm and 1000 to 2000 μm etc., are used.

The granulates of the bone formation agent according to the invention can have, depending on their use, a substantially non-uniform, irregular, polygonal geometric shape, but also can have a substantially uniform geometric shape, for example a spherical shape.

A further feature, according to the invention, of the bone formation agent in the form of a granulate is matching of the pore diameter to the granulate diameter. Advantageous mechanical properties are accordingly achieved for granulates when the average pore size diameters in the upper size range, that is to say in pore size distribution (III) or, when (III) is absent, in pore size distribution (II), do not exceed 50% of the average granulate size of the granulate fraction in question. Accordingly, the maximum of the pore size of pore size distributions (II) or (III) preferably lies in a size range from 10 to 50% of the average granulate size of a granulate fraction.

The requirements for the bone formation agent differ according to whether it is used in the form of a granulate or in the form of a shaped piece. Because higher mechanical demands are usually made of shaped pieces than of granulates, the shares of pore size distribution (III) are in that case reduced in accordance with the invention in favour of pore size distribution (II). In the case of particular embodiments of the bone formation agent as shaped pieces, statistical pores of pore size distribution (III) and/or defined pores in the form of tubular pores are even dispensed with altogether. In the case of granulates having a desired small average granulate size, statistical pores of pore size distribution (III) will also be dispensed with because of the size limitation. In that case, matching of the pore size to the granulate size is carried out by means of pore size distribution (II).

In addition to a granular geometric shape, the bone formation agent can also be present in the form of a shaped piece having a precisely defined geometric shape. The bone formation agent in the form of a shaped piece having a specific geometry is manufactured by machining on computer-controlled machines. By that means any desired geometric shapes can be produced, preferably cubes, cuboids, cylinders, wedges and similar pieces. However, unworked sintered pieces can also be used to manufacture individual implants for a specific patient or implants for particular indications, for example trepanation closures, fillers for cages in spine surgery, alveolar augmentations for the dental sector and others besides. In that case there are practically no limits to the variety of shapes.

In addition to the statistical porosity having discrete pore size distributions it is also possible to introduce a defined porosity—in the form of tubular pores—into shaped bodies by means of machining. The orientation of those tubular pores is preferably matched to the bone growth direction and accordingly promotes the growth of bone into the shaped body. Depending on the mechanical demands on the shaped body, one-, two- or three-dimensional bore patterns can be introduced into the shaped body. That defined porosity is preferably in a diameter range from 0.5 to 2 mm. The overall porosity of statistical and defined porosity should not exceed 85% by volume for reasons of strength.

In accordance with the invention, the pore size distribution over the cross-section of a shaped body is constant and/or variable. For increasing the mechanical strength of a shaped body whilst providing an appropriate overall porosity, the shaped body is, in a peripheral region, made up of a dense structure and comprises only pores of pore size distribution (I) and/or (II) whereas its interior has, in accordance with the invention, a combination of all forms of the statistical porosity. The structure of such a shaped body is then brought closer to the nature of natural bone. Depending on the mechanical stressing, a defined tubular porosity in one-, two- or three-dimensional form can be additionally superimposed on such a shaped body. The overall porosity in the peripheral zone should in that case not exceed a value of 35% by volume, whereas in the interior of the shaped body the overall porosity is limited to 85% by volume. The thickness of the zones is variable and encompasses a range from 10 to 40% of the maximum dimension perpendicular to the tensile stress or parallel to the bending stress of the shaped piece for the peripheral zone and 60 to 90% for the core zone.

In a particular embodiment of the invention it is also possible to use the bone formation agent in combination with various active ingredients, for example antibacterial substances, substances that promote wound healing such as PRP, hyaluronic acid inter alia, bone-growth-promoting active ingredients and/or anticoagulant active ingredients such as heparin. A very great variety of combinations are feasible in such cases. The active ingredients can be applied to the surface, in which case they have a short phase of action; they can also, however, completely fill the entire pore structure, in which case they act for a longer period by virtue of the high capillary forces. The type of application and the selection of the active ingredient or active ingredient combination will preferably be carried out in such cases in dependence on the particular indication.

The invention furthermore relates to a method of producing a bone formation agent, based on calcium phosphate, having an isotropic sintered structure and, between the sintered particles, statistically distributed pores in a plurality of discrete size distributions. The method is based on a synthesis route by way of a thermally induced solid-state reaction beginning with starting materials known per se. For production, to a mixture of previously synthesised calcium phosphate with a proportion of a mixture of its unreacted starting materials there are added, after intensive homogenisation, at least two porosity-causing agents that can be burnt off, the amounts and particle distributions thereof being such that in each case they increase or produce the share of one of the two desired discrete pore size distributions. The calcium phosphate constituents and porosity-causing agents are homogeneously mixed together without further particle comminution and compacted, the porosity-causing agents are removed by heating and the porous non-fired bodies are heated to reaction/sintering temperature for the requisite time. The fired bodies are subsequently cooled down to room temperature and the porous calcium phosphate obtained is comminuted in accordance with the desired granulate size or is processed into shaped bodies.

A particular embodiment of the method uses preferably three particle fractions of porosity-causing agents that can be burnt off, which are graduated in their relative amounts and their particle size distributions, in order to produce pores in three discrete pore size distributions in the porous calcium phosphate.

The calcium phosphate is preferably beta-tricalcium phosphate having a phase purity with respect to hydroxyapatite that is greater than or equal to 99% by weight. The unreacted starting materials (A) and (B) are, in that case, calcium carbonate $CaCO_3$ and calcium hydrogen phosphate $CaHPO_4$; starting material (C) is previously synthesised beta-tricalcium phosphate. Before mixing with the unreacted starting materials (A) and (B) in a molar ratio of 1:2, the synthesised beta-tricalcium phosphate is comminuted to a particle size<63 μm, with a $d_{50}$ value in the range from 5 to 20 μm. Such a particle size band ensures that the majority of powder particles subjected to sintering are above the phagocytable size range. In conjunction with the amount of unreacted starting components, the remaining fines content results in a strong sintering bond for the particles of beta-tricalcium phosphate.

In order to produce, for example, tricalcium phosphate having an isotropic sintered structure and statistically distributed pores in a plurality of discrete size distributions by way of the synthesis route of a thermally induced solid-state reaction beginning with starting materials known per se, the previously synthesised starting material (C) is used as the starting point, to which there is added an appropriate proportion of the mixture of its unreacted starting materials (A) and (B) in a molar ratio of 1:2, the mixture is intensively homogenised and subsequently at least two (starting materials (D) and (E)), preferably three (starting materials (D) to (F)), porosity-causing agents that can be burnt off are added in amounts and particle distributions such that in each case they increase or produce the share of the desired number of discrete pore size distributions. The mixture of calcium phosphate constituents and porosity-causing agents is homogenised without further particle comminution and compacted, the porosity-causing agents are removed by heating and the porous bodies are subjected to reaction/sinter firing.

The addition of a proportion of the mixture of the unreacted starting materials (A) and (B) in a molar ratio of 1:2 to the previously synthesised starting material (C) serves on the one hand to increase the interconnecting porosity having the pore size distribution (I) but also on the other hand to improve the sintering behaviour of the previously synthesised starting material (C), consequently resulting in improved mechanical strength of the porous beta-tricalcium phosphate, and, in accordance with the invention, is added to the mixture in a proportion in terms of amount in the range from 1 to 50% by weight, based on the amount of starting material (C) used.

Depending on the intended use of the bone formation agent, to the mixture of the previously synthesised starting material (C) with the proportion of the mixture of its unreacted starting materials (A) and (B) in a ratio of 1:2, there are additionally added porosity-causing agents that can be burnt off, in defined particle size distributions and proportions in terms of amount so as to obtain the desired shares of pores in size distributions (I), (II) and (III).

Porosity-causing agents that come into consideration include any substances that can be burnt off or volatilised, that can be comminuted well and that can be worked up into discrete particle size distributions. In principle it is possible to achieve the three pore size distributions using chemically identical or also different porosity-causing agents. Because of their prior history, the porosity-causing agents have a substantially non-uniform geometric shape which can be described as irregular or polygonal and their size distribution is in the desired pore size range since on being burnt off they leave behind a hollow space that substantially corresponds to their original shape and size. For pore size distribution (I) there is used, besides the unreacted stoichiometric mixture of starting materials, a porosity-causing agent having a $d_{50}$ value in the range from 0.5 to 10 μm, for pore size distribution (II) a porosity-causing agent having a $d_{50}$ value in the range from 10 to 100 μm and for pore size distribution (III) a porosity-causing agent having a $d_{50}$ value in the range from 100 to 5000 μm.

The unreacted stoichiometric mixture of starting materials for synthesising the calcium phosphate is used, for increasing the pore size distribution (I), in a proportion in terms of amount of from 1 to 50% by weight. During the reaction/sinter firing, it is converted into the desired calcium phosphate without adversely affecting the purity thereof. It increases the share of pores in the range of pore size distribution (I) and at the same time results in strengthening of the sintered structure of calcium phosphate.

As a porosity-causing agent that can be burnt off to produce the bone formation agent according to the invention, ammonium hydrogen carbonate, in particular, has been found to be suitable. In order to increase pore size distribution (I), it is added to the mixture of calcium phosphate constituents in the form of a particle fraction having a $d_{50}$ value in the range from 0.5 to 10 μm in an amount of from 1 to 20% by weight. To produce pore size distribution (II) ammonium hydrogen carbonate having a $d_{50}$ value in the range from 10 to 100 μm is added in an amount of from 5 to 40% by weight, whereas to produce pore size distribution (III) a particle fraction thereof having a $d_{50}$ value in the range from 100 to 5000 μm is added in an amount of from 1 to 40% by weight. The amounts of porosity-causing agent used are calculated with respect to the amount of calcium phosphate used.

In addition to intensive homogenisation of the mixture of calcium phosphate constituents and the homogenisation thereof—without further particle comminution—with the porosity-causing agents that can be burnt off, compacting is above all of crucial significance for the production of unworked pieces to be machined. In this case, in the course of experimentation tests on standard samples, an isostatic compression method with compression pressures in the range from 100 to 250 MPa has been found to be advantageous.

The compacted mixture of the calcium phosphate constituents and porosity-causing agents is subjected to a controlled heat treatment, also where appropriate in a plurality of treatment steps, wherein the porosity-causing agents are removed by sublimation or are burnt off, the unreacted starting materials react in their stoichiometric ratio to form the desired calcium phosphate, and the powder particles of calcium phosphate used practically "cement together" and form strong sintering necks. At the same time, the presence of the powder particles of the desired calcium phosphate promotes the formation of that phase from the unreacted starting raw materials by means of appropriate seed formation and crystallisation, so that a high phase purity of the calcium phosphate formed of more than 99% by weight is achieved.

The heat treatment of the compacted mixture is carried out by both controlled heating and cooling programmes, in conjunction with holding steps in relevant temperature ranges. As heating and cooling rates, values in the range from 0.5 to 5 K/min have been found to be advantageous. The more compact and massive the sintered pieces, the lower the heating and cooling rate selected for use. Suitable holding temperatures for a sintered structure for high mechanical demands are in the range from 1373 to 1573 K, the selected level of sintering temperature being governed by the added amount of the stoichiometric mixture of unreacted starting materials. As the amount of that mixture increases, the sintering temperature can be moved to lower values in order to achieve comparable mechanical strength in the sintered bodies. In the particular case of the production of beta-tricalcium phosphate it can also be advantageous, for phase purity, to introduce a further holding step in the range from 1123 to 1223 K in order to make sure that phase constituents of alpha-tricalcium phosphate are excluded.

In accordance with a further embodiment, the invention relates to a bone formation agent of calcium phosphate having an overall porosity composed of a plurality of pore size distribution ranges, characterised in that it comprises an overall porosity that is irregular in its geometric shape consisting of at least two, preferably three, discrete ranges of pore sizes that are statistically distributed in terms of their size, in that the calcium phosphate has a primary particle size smaller than 63 μm with a $d_{50}$ value in the range from 5 to 20 μm and in that the share of interconnecting pores in the overall porosity is limited to pore sizes smaller than 10 μm.

The bone formation agent can be characterised in that the maxima of the three discrete pore size distribution ranges are in the diameter ranges 0.5 to 10 μm (I), 10 to 100 μm (II) and 100 to 5000 μm (III).

Furthermore, the bone formation agent can be characterised in that the volume ratios of the three discrete pore size distributions are in the range from 20 to 40% by volume for pore size distribution (I), in the range from 5 to 40% by volume for pore size distribution (II) and in the range from 1 and especially 5 to 40% by volume for pore size distribution (III), the overall porosity not exceeding a figure of 80 and especially 85% by volume.

Furthermore, the bone formation agent can be characterised in that the calcium phosphate consists to a substantial extent, and especially to an extent of at least 95%, of alpha-tricalcium phosphate, beta-tricalcium phosphate, octacalcium phosphate, alkali metal-modified and/or alkaline earth metal-modified tricalcium phosphate, calcium diphosphate, carbonate apatite of type B, calcium-deficient hydroxyapatite or mixtures thereof.

Furthermore, the bone formation agent can be characterised in that the calcium phosphate consists preferably of beta-tricalcium phosphate having a phase purity of ≥99% by weight, relative to the foreign hydroxyapatite phase.

Furthermore, the bone formation agent can be characterised in that it is in the form of a granulate and is present in various, indication-related granulate fractions in a size range between 50 and 10000 μm.

Furthermore, the bone formation agent can be characterised in that the granulate has a substantially non-uniform geometric shape.

Furthermore, the bone formation agent can be characterised in that the granulate has a substantially uniform geometric shape.

Furthermore, the bone formation agent can be characterised in that the granulate has a substantially spherical shape.

Furthermore, the bone formation agent can be characterised in that pore size distributions (II) or (III) are matched to the granulate size, the average pore size amounting to less than half the average granulate size of the granulate fraction in question and preferably being in a range from 10 to 50% of the average granulate size.

Furthermore, the bone formation agent can be characterised in that it is in the form of a shaped body having a defined geometric design.

Furthermore, the bone formation agent can be characterised in that in addition to a statistical porosity it has a defined porosity in the form of tubular pores, especially of type (III).

Furthermore, the bone formation agent can be characterised in that the defined porosity is formed by one-, two- or three-dimensional bores, introduced by machining, in the diameter range from 0.5 to 2 mm, and the overall porosity consisting of statistical and tubular porosity does not exceed a value of 85% by volume.

Furthermore, the bone formation agent can be characterised in that the compact shaped body has a pore size distribution graduated in size and shape from the periphery to the core, with preferably in the peripheral zone pore size distributions (I) and/or (II) being present especially with an overall porosity of up to 35% by volume and in the core zone pore size distributions (I) and/or (II) and/or (III) being present especially up to an overall porosity of 85% by volume, with especially the peripheral zone having a range from 10% to 40% and the core zone from 60% to 90% of the largest dimension of the implant perpendicular to the tensile stress direction or parallel to the bending stress.

Furthermore, the bone formation agent can be characterised in that it has, on its surface and/or in its internal pore structure, antibacterial, wound healing-promoting, bone growth-promoting and/or anticoagulant substances in suitable effective concentrations.

Furthermore, the bone formation agent can be characterised in that it has a shape individually made for a particular patient.

Furthermore, the bone formation agent can be characterised in that it is present in standardised dimensions and shapes, preferably in the form of a cube, cuboid, cylinder or wedge.

Furthermore, the bone formation agent can be characterised in that it has an indication-related shape, preferably in the form of a trepanation closure, alveolar augmentation or filler for cages for vertebrae replacement.

According to a further embodiment, the invention relates to a method of producing a bone formation agent consisting of calcium phosphate by way of the synthesis route of a thermally induced solid-state reaction beginning with a stoichiometric mixture of two preferably known starting materials (1, 2), their homogeneous mixing, sintering and comminution, and subsequent admixture with porosity-causing agents that can be burned off or that are volatilised, characterised in that to the calcium phosphate (C) synthesised from the starting materials (1, 2), after production and comminution, there are added, for production of a microporosity, a further proportion of the unreacted stoichiometric mixture of the starting materials (1, 2) and at least two further porosity-causing agents that can be burnt off to increase pore share (I) according to claim 2 and to produce a pore share (II), but preferably three further porosity-causing agents that can be burnt off to increase pore share (I) and to produce pore shares (II) and (Ill) according to claim 3, and the mixture is homogenised, compacted and fired to form a porous sintered body.

The method can be characterised in that to the calcium phosphate (C), produced from the starting materials (1, 2), there is added the unreacted stoichiometric mixture of the starting materials (1, 2) in an amount between 1 and 50% by weight, based on the amount of calcium phosphate.

Furthermore, the method can be characterised in that the calcium phosphate (C) is tricalcium phosphate, preferably beta-tricalcium phosphate having a phase purity of ≥99% by weight, and the starting materials (1, 2) are calcium carbonate and calcium hydrogen phosphate.

Furthermore, the method can be characterised in that the calcium phosphate introduced into the mixture has a primary particle size smaller than 63 µm with a $d_{50}$ value in the range from 5 to 20 µm.

Furthermore, the method can be characterised in that the added porosity-causing agents that can be burnt off or that are volatilised have identical or different chemical natures and are added in particle fractions having $d_{50}$ values in the range from 0.5 to 10 µm, 10 to 100 µm and 100 to 5000 µm.

Furthermore, the method can be characterised in that there is added to the calcium phosphate mixture, when using the porosity-causing agent ammonium hydrogen carbonate, the particle fraction having a $d_{50}$ value in the range from 0.5 to 10 µm in an amount of from 1 to 20% by weight, the particle fraction having a $d_{50}$ value in the range from 10 to 100 µm in an amount of from 5 to 40% by weight and the particle fraction having a $d_{50}$ value in the range from 100 to 5000 µm in an amount of from 1 to 40% by weight, based on the calculated amount of calcium phosphate.

Furthermore, the method can be characterised in that the compacting of the mixture of calcium phosphate (C) with the proportion of the unreacted stoichiometric mixture of starting materials (1, 2) and the porosity-causing agents is carried out isostatically under a compression pressure of from 100 to 250 MPa.

Furthermore, the method can be characterised in that the compacted mixture of the calcium phosphate(s) (C) with the stoichiometric mixture of the unreacted starting materials (1, 2) and the porosity-causing agent(s) that can be burnt off is heated at a heating rate in the range from 0.5 to 5 K/min to the range from 1373 to 1573 K, is held at that temperature for preferably from 24 to 72 hours and is then cooled back down to room temperature at a cooling rate of from 0.5 to 5 K/min.

Furthermore, the method can be characterised in that, in the controlled temperature treatment, an additional temperature-holding step in the range from 1123 to 1223 K is used.

Figure 4:
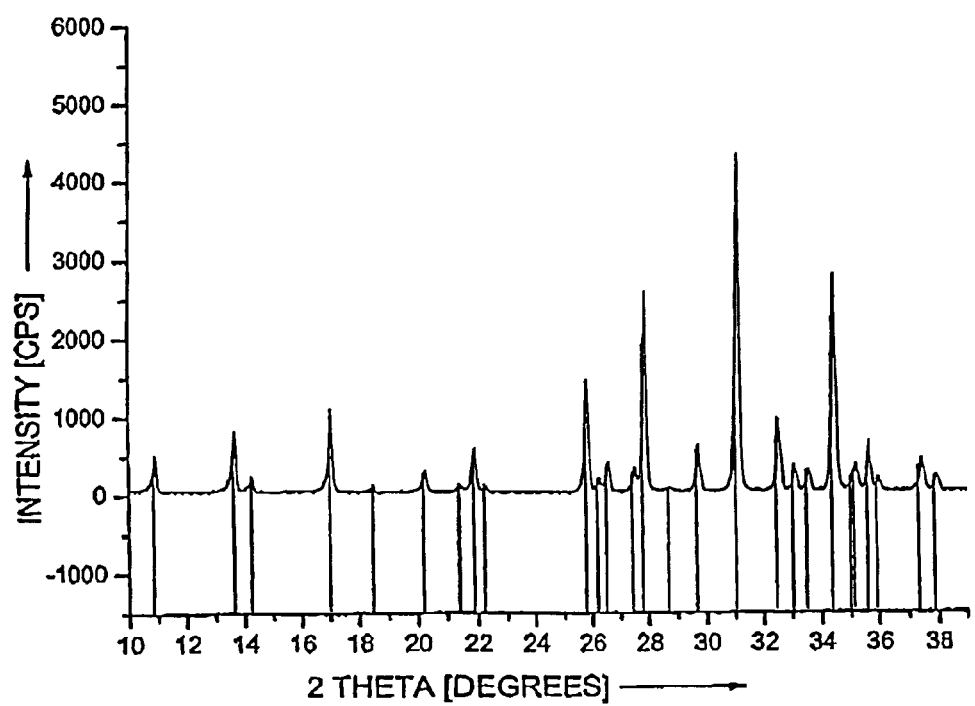

FIG. 4 demonstrates the phase purity of the beta-tricalcium phosphate used of more than 99% by weight, relative to the hydroxyapatite phase.

Figure 5:
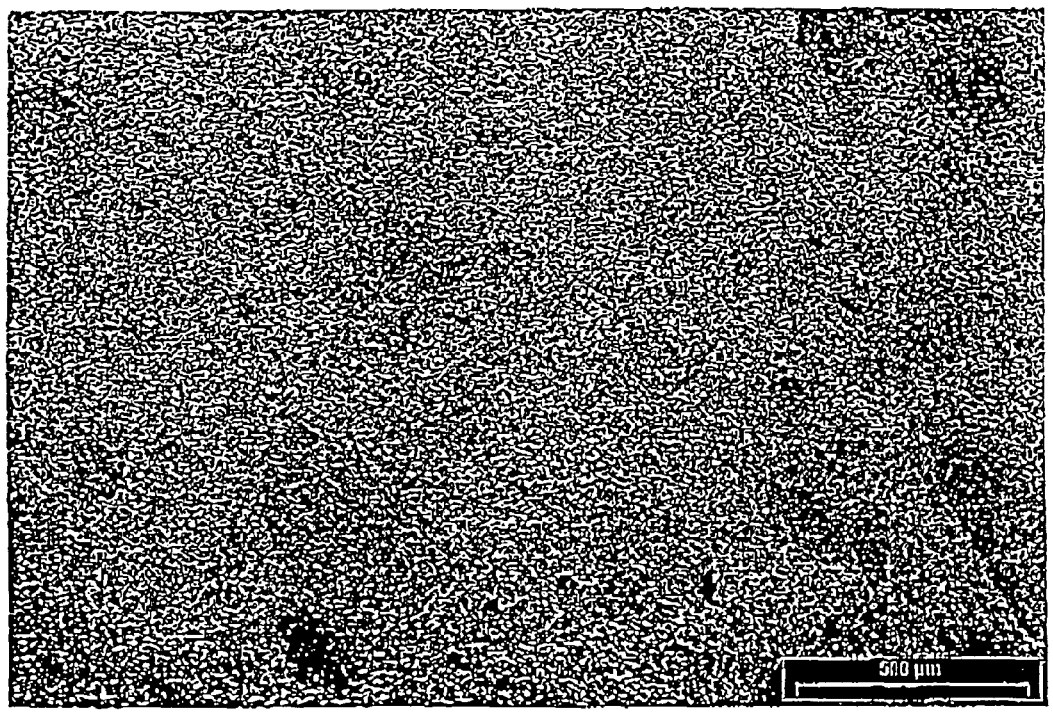

FIG. 5 illustrates the closed-cell sintered structure of a granulate particle at a freshly broken surface, by means of REM.

Figure 6:
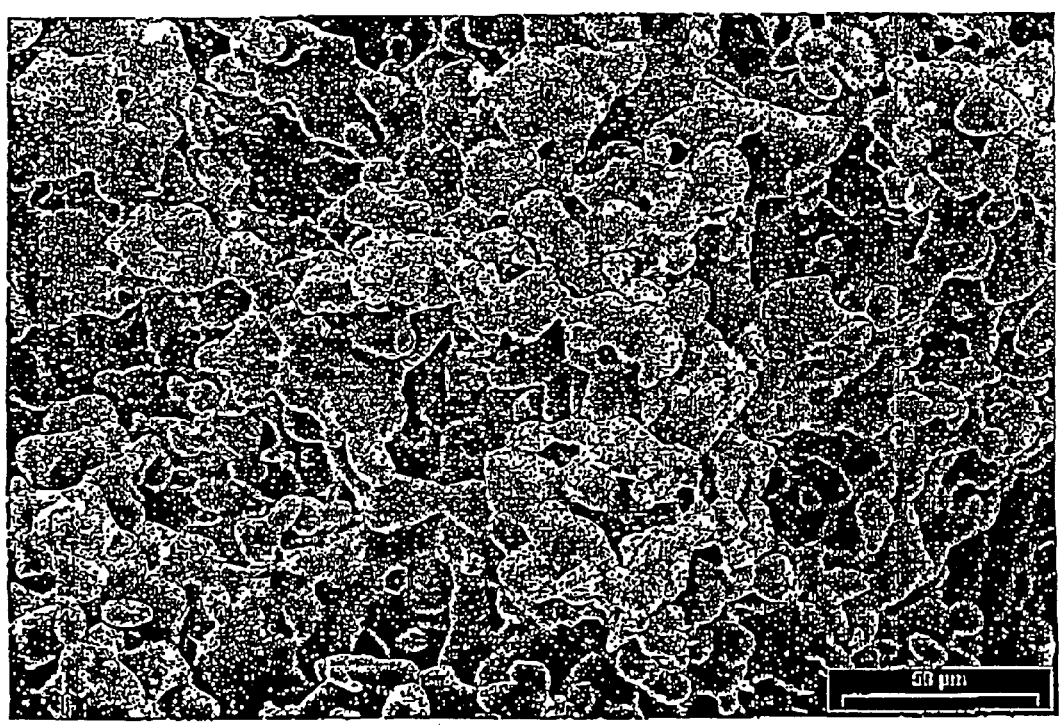

FIG. 6 shows the interconnecting micropore system of less than 10 µm together with individual pores of size 30 to 50 µm linked by way of that network, at a freshly broken surface of a granulate particle.

FIG. 7 illustrates a typical curve of pore size distributions (I) and (II) having two maxima in the range <100 µm, measured by means of mercury porosimetry.

The invention will be described hereinbelow using selected implementation examples. For the preparation of, by way of example, porous beta-tricalcium phosphate, starting materials (A) to (F) are provided:

Starting material (A): calcium carbonate, $CaCO_3$, analytical grade, in powder form, dry Starting material (B): calcium hydrogen phosphate, $CaHPO_4$, analytical grade, in powder form, dry Starting material (C): pure-phase beta-tricalcium phosphate, Ca, $Ca_3(PO_4)_2$, in powder form, dry, less than 63 µm ($d_{50}$ equal to 12 µm)

Starting material (D): ammonium hydrogen carbonate, analytical grade, having a $d_{50}$ value in the range from 0.5 to 10 µm Starting material (E): ammonium hydrogen carbonate, analytical grade, having a $d_{50}$ value in the range from 10 to 100 µm Starting material (F): ammonium hydrogen carbonate, analytical grade, having a $d_{50}$ value in the range from 100 to 5000 µm

IMPLEMENTATION EXAMPLE 0

To produce starting material (C), the starting materials (A) and (B) are homogeneously mixed together in a molar ratio of 1:2. The mixture is compacted using a pressure of 150 MPa and heated over a period of 20 hours at 1200° C. under normal atmosphere. The resulting reaction product, beta-tricalcium phosphate, has a phase purity of >99%, is comminuted and fractionated to a particle size <63 µm and is then available as starting material (C) for the further procedures.

IMPLEMENTATION EXAMPLE 1

10% by weight of a mixture of starting materials (A) and (B) in a molar ratio of 1:2 are added to starting material (C) and all the constituents are thoroughly mixed with one another. Subsequently, 10% by weight of starting material (D) having a $d_{50}$ value of 8 µm, 35% by weight of starting material (E) having a $d_{50}$ value of 35 µm and 5% by weight of starting material (F) having a $d_{50}$ value of 350 µm are added to the mixture and mixed in.

The mixture is compacted by means of a pressure of 150 MPa and the starting materials (D), (E) and (F) are removed by sublimation over 20 hours at 80° C. at normal atmosphere. The compacted porous material is then sintered at 1200° C. over 20 hours at normal atmosphere and subsequently broken up into a particle fraction of from 500 to 1000 µm. For rounding of the corners, the granulate is rotated on its own in a PE bottle on a roller stand at a speed of rotation of 30 rev/min and is then classified into individual particle fractions.

Figure 1:
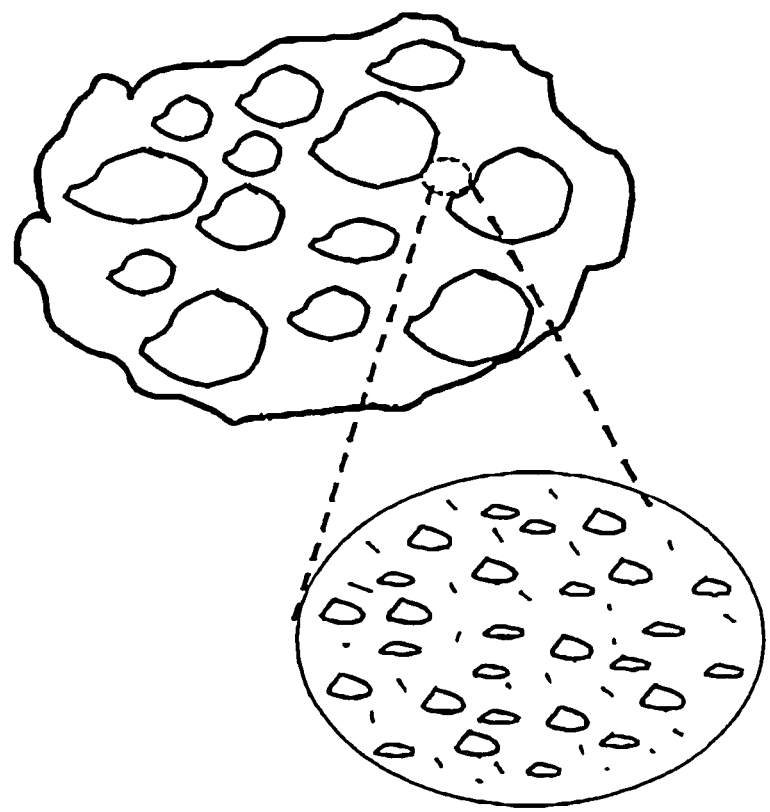
FIG. 1 shows, in diagrammatic form, an example of a bone formation agent according to the invention, having three pore size distributions (I), (II) and (III).

The resulting granulate particles have an overall porosity of 72%. The bulk densities of the granulate particles produced by this method are 0.9 g/cm³. The bulk density of compacted material without additional porosity-causing agents is, on average, 1.2 g/cm³. The granulate particles have a pore structure having three discrete pore size distributions in accordance with FIG. 1.

IMPLEMENTATION EXAMPLE 2

20% by weight of a mixture of starting materials (A) and (B) in a molar ratio of 1:2 are added to starting material (C) and all the constituents are thoroughly mixed with one another. Subsequently, 20% by weight of starting material (D) having a $d_{50}$ value of 8 µm, 25% by weight of starting material (E) having a $d_{50}$ value of 35 µm and 10% by weight of starting material (F) having a $d_{50}$ value of 250 µm are added to the mixture and mixed in.

The mixture is compacted by means of a pressure of 170 MPa and the starting materials (D), (E) and (F) are removed by sublimation over 20 hours at 80° C. at normal atmosphere. The compacted porous material is then sintered at 1200° C over 20 hours at normal atmosphere and subsequently broken up into a particle fraction of from 500 to 1000 µm. For rounding of the corners, the granulate is rotated on its own in a PE bottle on a roller stand at a speed of rotation of 30 rev/min and is then classified into individual particle fractions.

The resulting granulate particles have an overall porosity of 78%. The bulk densities of the granulate particles produced by this method are 0.8 g/cm³. The bulk density of compacted material without additional porosity-causing agents is, on average, 1.2 g/cm³. The granulate particles have a pore structure having three discrete pore size distributions in accordance with FIG. 1.

IMPLEMENTATION EXAMPLE 3

30% by weight of a mixture of starting materials (A) and (B) in a molar ratio of 1:2 are added to starting material (C) and all the constituents are thoroughly mixed with one another. Subsequently, 20% by weight of starting material (D) having a $d_{50}$ value of 6.5 µm, 5% by weight of starting material (E) having a $d_{50}$ value of 65 µm and 20% by weight of starting material (F) having a $d_{50}$ value of 650 µm are added to the mixture and mixed in.

The mixture is compacted by means of a pressure of 170 MPa and the starting materials (D), (E) and (F) are removed by sublimation over 20 hours at 80° C. at normal atmosphere. The compacted porous material is then sintered at 1200° C. over 20 hours at normal atmosphere and subsequently broken up into a particle fraction of from 1000 to 2000 µm. For rounding of the corners, the granulate is rotated on its own in a PE bottle on a roller stand at a speed of rotation of 30 rev/min and is then classified into individual particle fractions.

The resulting granulate particles have an overall porosity of 70%. The bulk densities of the granulate particles produced by this method are 0.9 g/cm³. The bulk density of compacted material without additional porosity-causing agents is, on average, 1.2 g/cm³. The granulate particles have a pore structure having three discrete pore size distributions in accordance with FIG. 1.

IMPLEMENTATION EXAMPLE 4

40% by weight of a mixture of starting materials (A) and (B) in a molar ratio of 1:2 are added to starting material (C) and all the constituents are thoroughly mixed with one another. Subsequently, 5% by weight of starting material (D) having a $d_{50}$ value of 5 µm, 15% by weight of starting material (E) having a $d_{50}$ value of 65 µm and 35% by weight of starting material (F) having a $d_{50}$ value of 650 µm are added to the mixture and mixed in.

The mixture is compacted by means of a pressure of 180 MPa and the starting materials (D), (E) and (F) are removed by sublimation over 20 hours at 80° C. at normal atmosphere. The compacted porous material is then sintered at 1200° C. over 20 hours at normal atmosphere and subsequently broken up into a particle fraction of from 500 to 1000 µm. For rounding of the corners, the granulate is rotated on its own in a PE bottle on a roller stand at a speed of rotation of 30 rev/min and is then classified into individual particle fractions.

The resulting granulate particles have an overall porosity of 81%. The bulk densities of the granulate particles produced by this method are 0.8 g/cm³. The bulk density of compacted material without additional porosity-causing agents is, on average, 1.2 g/cm³. The granulate particles have a pore structure having three discrete pore size distributions in accordance with FIG. 1.

IMPLEMENTATION EXAMPLE 5

25% by weight of a mixture of starting materials (A) and (B) in a molar ratio of 1:2 are added to starting material (C) and all the constituents are thoroughly mixed with one another. Subsequently, 15% by weight of starting material (D) having a $d_{50}$ value of 5 µm, 15% by weight of starting material (E) having a $d_{50}$ value of 85 µm and 15% by weight of starting material (F) having a $d_{50}$ value of 1850 µm are added to the mixture and thoroughly mixed in.

The mixture is compacted by means of a pressure of 190 MPa and the starting materials (D), (E) and (F) are removed by sublimation over 20 hours at 80° C. at normal atmosphere. The compacted porous material is then sintered at 1200° C. over 20 hours at normal atmosphere and subsequently broken up into a particle fraction of from 3200 to 5000 µm. For rounding of the corners, the granulate is rotated on its own in a PE bottle on a roller stand at a speed of rotation of 30 rev/min and is then classified into individual particle fractions.

The resulting granulate particles have an overall porosity of 69%. The bulk densities of the granulate particles produced by this method are 0.9 g/cm³. The bulk density of compacted material without additional porosity-causing agents is, on average, 1.2 g/cm³. The granulate particles have a pore structure having three discrete pore size distributions in accordance with FIG. 1.

IMPLEMENTATION EXAMPLE 6

20% by weight of a mixture of starting materials (A) and (B) in a molar ratio of 1:2 are added to starting material (C) and all the constituents are thoroughly mixed with one another. Subsequently, 20% by weight of starting material (D) having a $d_{50}$ value of 5 µm, 20% by weight of starting material (E) having a $d_{50}$ value of 65 µm and 10% by weight of starting material (F) having a $d_{50}$ value of 250 µm are added to the mixture and thoroughly mixed in.

The mixture is compacted by means of a pressure of 200 MPa and the starting materials (D), (E) and (F) are removed by sublimation over 20 hours at 80° C. at normal atmosphere. The compacted porous material is then sintered at 1200° C. over 20 hours at normal atmosphere. The porous basic bodies thereby produced are mechanically processed into cylinders, cuboids and cubes.

The density of the ceramic material before removal of starting materials (D), (E) and (F) by sublimation is, on average, 1.6 g/cm³ and thereafter, on average, 0.8 g/cm³. The overall porosity was 73%. The shaped bodies have three discrete pore size distributions in accordance with FIG. 1.

IMPLEMENTATION EXAMPLE 7

20% by weight of a mixture of starting materials (A) and (B) in a molar ratio of 1:2 are added to starting material (C) and all the constituents are thoroughly mixed with one another. Subsequently, 25% by weight of starting material (D) having a $d_{50}$ value of 8 µm, 20% by weight of starting-material (E) having a $d_{50}$ value of 35 µm and 15% by weight of starting material (F) having a $d_{50}$ value of 350 µm are added to the mixture and thoroughly mixed in.

The mixture is compacted by means of a pressure of 200 MPa and the starting materials (D), (E) and (F) are removed by sublimation over 20 hours at 80° C. at normal atmosphere. The compacted porous material is then sintered at 1200° C. over 20 hours at normal atmosphere. The porous basic bodies thereby produced are mechanically processed into wedges, trepanation closures and alveolar augmentations.

The density of the ceramic material before removal of starting materials (D), (E) and (F) by sublimation is, on average, 1.6 g/cm³ and thereafter, on average, 0.6 g/cm³. The overall porosity was 83%. The shaped bodies have three discrete pore size distributions in accordance with FIG. 1.

IMPLEMENTATION EXAMPLE 8

30% by weight of a mixture of starting materials (A) and (B) in a molar ratio of 1:2 are added to starting material (C) and all the constituents are thoroughly mixed with one another. Subsequently, 15% by weight of starting material (D) having a $d_{50}$ value of 4 µm, 5% by weight of starting material (E) having a $d_{50}$ value of 85 µm and 5% by weight of starting material (F) having a $d_{50}$ value of 250 µm are added to the mixture and thoroughly mixed in.

The mixture is compacted by means of a pressure of 250 MPa and the starting materials (D), (E) and (F) are removed by sublimation over 20 hours at 80° C. at normal atmosphere. The compacted porous material is then sintered at 1200° C. over 20 hours at normal atmosphere. The porous basic bodies thereby produced are mechanically processed into cylinders, cuboids and cubes and provided with a three-dimensional bore pattern having a bore diameter of 1 mm.

The density of the ceramic material before removal of starting materials (D), (E) and (F) by sublimation is, on average, 1.6 g/cm³ and thereafter, on average, 1.4 g/cm³. After incorporation of the defined tubular porosity, the overall porosity consisting of statistical and defined porosity was 75%. The shaped bodies have, in addition to the defined tubular porosity, three discrete pore size distributions in accordance with FIG. 1.

IMPLEMENTATION EXAMPLE 9

30% by weight of a mixture of starting materials (A) and (B) in a molar ratio of 1:2 are added to starting material (C) and all the constituents are thoroughly mixed with one another.

The mixture is divided up into 3 sub-portions. To sub-portion (1) there are added 5% by weight of starting material (D) having a $d_{50}$ value of 4 µm and 10% by weight of starting material (E) having a $d_{50}$ value of 35 µm, to sub-portion (2) 10% by weight of starting material (D) having a $d_{50}$ value of 6.5 µm and 20% by weight of starting material (E) having a $d_{50}$ value of 65 µm, and to sub-portion (3) there are added 20% by weight of starting material (D) having a $d_{50}$ value of 8 µm, 20% by weight of starting material (E) having a $d_{50}$ value of 85 µm and 20% by weight of starting material (F) having a $d_{50}$ value of 650 µm, and the sub-portions, separately, are thoroughly mixed.

Figure 2:
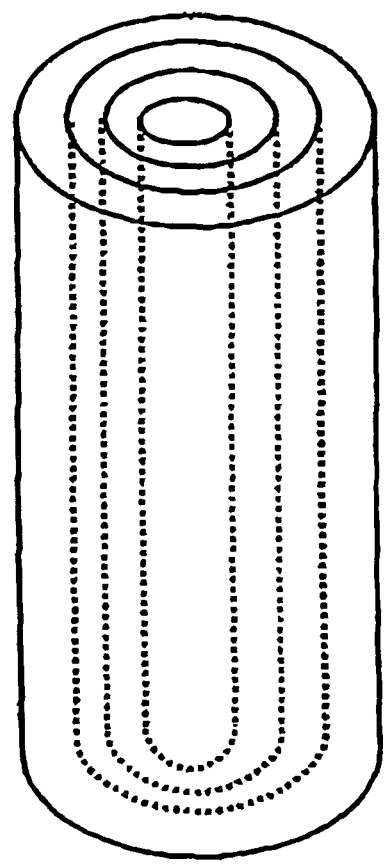
FIGS. 2 and 3 illustrate the production of a graduated material having a density that decreases, or porosity that increases, from the outside to the inside, in accordance with Implementation Example 8.

A flexible compression mould for cold isostatic compression is provided with two tubes having the desired spacing from one another (see FIG. 2), inserted one into the other. The sub-portions are filled into the resulting spacings in such a manner that the amounts of added starting materials (D), (E) and (F) decrease from the inside to the outside. After filling has been carried out, the tubes are carefully removed so that only superficial powder mixing of the individual sub-portions takes place.

The material is compacted in the flexible compression mould by means of a pressure of 200 MPa and the starting materials (D), (E) and (F) are removed by sublimation over 20 hours at 80° C. at normal atmosphere. The compacted porous material is then sintered at 1200° C. over 20 hours at normal atmosphere. The porous basic bodies thereby produced are mechanically processed to form shaped bodies according to Implementation Examples 6 to 8.

Figure 3:
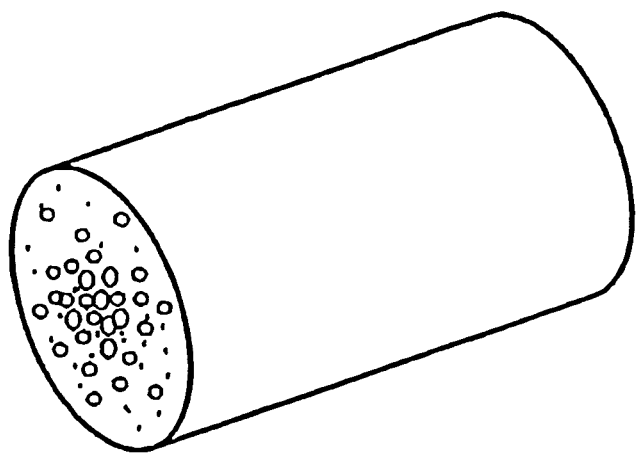

A graduated material is formed, the porosity of which increases from the outside to the inside. As a result, an increased mechanical loading capacity can be established, as well as locally different resorption rates (see FIG. 3).

IMPLEMENTATION EXAMPLE 10

In the case of a cylindrical part produced in accordance with Implementation Example 9, tubular pores having a diameter of 1.4 mm are additionally introduced in the peripheral zone of low porosity in the bone growth direction. As a result, the dense material region is opened up for bone to grow in more rapidly, without curtailing the good mechanical properties of the peripheral zone.

The invention claimed is:

1. A bone formation agent of porous pure-phase beta-tricalcium phosphate having an isotropic sintered structure and, between the sintered particles of the calcium phosphate, statistically distributed pores in a plurality of discrete size ranges, characterised in that the bone formation agent has a porosity composed of at least three discrete ranges of pore sizes (I) to (III), which are statistically distributed in terms of their size, and the maxima of the three discrete pore size distributions are at pore diameters in the ranges from 0.5 to 10 µm (I), 10 to 100 µm (II) and 100 to 5000 µm (III), the porosity has an irregular geometric shape, the sintered particles of the calcium phosphate have a particle size smaller than 63 μm with a d50 value in the range from 5 to 20 μm, the interconnecting pore share in the porosity is limited to pore sizes less than 10 μm, and said bone formation agent being in the form of a granulate where the maxima of the discrete pore size distributions (II) or (III) are less than half the average granulate size of a granulate fraction and are in a range between 10 and 50% of the average granulate size of the granulate fraction.

2. The bone formation agent according to claim 1, characterised in that the volume shares of the discrete pore size distributions (I) to (III) are in the range from 20 to 40% by volume for pore size distribution (I), in the range from 5 to 40% by volume for pore size distribution (II) and in the range from 1 to 40% by volume for pore size distribution (III), the overall porosity not exceeding 85% by volume.

3. The bone formation agent according to claim 1, characterised in that the calcium phosphate consists of beta-tricalcium phosphate having a phase purity of ≥99% by weight, relative to a foreign hydroxyapatite phase.

4. The bone formation agent according to claim 1, further comprising various granulate fractions in a size range between 50 and 10000 μm.

5. The bone formation agent according to claim 4, characterised in that the granulate has a substantially non-uniform geometric shape.

6. The bone formation agent according to claim 4, characterised in that the granulate has a substantially uniform geometric shape.

7. The bone formation agent according to claim 6, characterised in that the granulate has a substantially spherical shape.

8. A bone formation agent of porous pure-phase beta-tricalcium phosphate having an isotropic sintered structure and, between the sintered particles of the calcium phosphate, statistically distributed pores in a plurality of discrete size ranges, characterised in that the bone formation agent has a porosity composed of at least three discrete ranges of pore sizes (I) to (III), which are statistically distributed in terms of their size, and the maxima of the three discrete pore size distributions are at pore diameters in the ranges from 0.5 to 10 μm (I), 10 to 100 μm (II) and 100 to 5000 μm (III), the porosity has an irregular geometric shape, the sintered particles of the calcium phosphate have a particle size smaller than 63 μm with a d50 value in the range 5 to 20 μm, the interconnecting pore share in the porosity is limited to pore sizes less than 10 μm, and said bone formation agent is in the form of a shaped body having a defined geometric design.

9. The bone formation agent according to claim 8, characterised in that in addition to a statistical porosity, said bone formation has a defined tubular porosity in the form of tubular pores.

10. The bone formation agent according to claim 9, characterised in that the defined tubular porosity is formed by one-, two- or three-dimensional bores, introduced by machining, in the diameter range from 0.5 to 2 mm, and the overall porosity consisting of statistical and tubular porosity does not exceed a value of 85% by volume.

11. The bone formation agent according to claim 8, characterised in that the bone formation agent is a compact shaped body having a pore size distribution graduated in size and volume share from the periphery to the core, with the peripheral zone pore size distributions (I) and/or (II) being present with an overall porosity of up to 35% by volume and in the core zone pore size distributions (I) and/or (II) and/or (III) being present up to an overall porosity of 85% by volume, with the peripheral zone having a range from 10% to 40% and the core zone from 60% to 90% of the largest dimension of the implant perpendicular to the tensile stress direction or parallel to the bending stress.

12. The bone formation agent according to claim 1, characterised in that it has, on its surface and/or in its internal pore structure, antibacterial, wound healing-promoting, bone growth-promoting and/or anticoagulant substances in suitable effective concentrations.

13. The bone formation agent according to claim 8, characterised in that it has a shape individually made for a particular patient.

14. The bone formation agent according to claim 8, characterised in that it is present in standardised dimensions and shapes, preferably in the form of a cube, cuboid, cylinder or wedge.

15. The bone formation agent according to claim 8, characterised in that it has an indication-related shape in the form of a trepanation closure, alveolar augmentation or filler for cages for vertebrae replacement.

16. The bone formation agent according to claim 8 characterized in that it has on its surface and/or in its internal pore structure, antibacterial, wound healing promoting, bone growth promoting and/or anticoagulant substances in suitable effective concentrations.

* * * * *